United States Patent [19]

Shephard et al.

[11] 4,217,129
[45] * Aug. 12, 1980

[54] FUNGICIDAL AND HERBICIDAL TRIAZOLE KETONES

[75] Inventors: Margaret C. Shephard; Paul A. Worthington, both of Maidenhead, England

[73] Assignee: Imperial Chemical Industries Limited, London, England

[*] Notice: The portion of the term of this patent subsequent to Dec. 19, 1995, has been disclaimed.

[21] Appl. No.: 900,317

[22] Filed: Apr. 26, 1978

[30] Foreign Application Priority Data

May 5, 1977 [GB] United Kingdom ............... 18861/77

[51] Int. Cl.² .................... A01N 9/22; C07D 233/60; C07D 249/08
[52] U.S. Cl. .......................................... 71/76; 71/92; 424/245; 424/269; 424/273 R; 548/262; 548/341
[58] Field of Search ............... 260/308 R, 299; 548/341, 262; 424/269, 245, 273 R; 71/76, 92

[56] References Cited

U.S. PATENT DOCUMENTS

| | | | |
|---|---|---|---|
| 4,005,083 | 1/1977 | Büchel et al. | 260/299 |
| 4,130,409 | 12/1978 | Shephard et al. | 260/308 R |

Primary Examiner—Alton D. Rollins
Attorney, Agent, or Firm—Cushman, Darby & Cushman

[57] ABSTRACT

Compounds of formula:

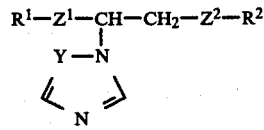

wherein $R^1$ and $R^2$ are alkyl, cycloalkyl or phenyl, Y is =N— or =CH— and one of $Z^1$ and $Z^2$ is carbonyl or a derivative thereof and the other is CHOH, or salts or metal complexes thereof. These compounds have fungicidal and plant growth regulating activity.

9 Claims, No Drawings

FUNGICIDAL AND HERBICIDAL TRIAZOLE KETONES

This invention relates to imidazole and triazole compounds useful as fungicides and plant growth regulating agents, to a process for preparing them, to fungicidal and plant growth regulating compositions containing them, to a method of combating fungal infections in plants using them and to a method of regulating the growth of plants using them.

The compounds have the general formula (I)

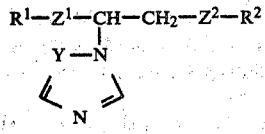

wherein each of $R^1$ and $R^2$, which may be the same or different, is unsubstituted or alkyl-substituted cycloalkyl unsubstituted or halo-substituted alkyl or unsubstituted or substituted phenyl, Y is =N— or =CH— and one of $Z^1$ and $Z^2$ is C=O or a derivative thereof (e.g. an imine, oxime, ketal, hydrazone or semicarbazone) and the other is —CH(OH)—; or an ester, ether, acid addition salt or metal complex thereof.

The compounds of the invention contain chiral centres. The compounds are generally obtained in the form of racemic mixtures. However, these and other mixtures can be separated into the individual isomers by methods known in the art e.g. chromatography. In many cases, the compounds can be prepared stereospecifically in the form of a single diastereoisomer.

The alkyl groups, which can be straight or branched chain, preferably have 1 to 5 carbon atoms; examples are methyl, ethyl, propyl (n- or i-propyl) and butyl (n-, i- or t-butyl).

Suitable substituents for the phenyl group are halogen, $C_{1-4}$ alkyl [e.g. methyl, ethyl, propyl (n- or i-propyl) and butyl (n-, i- or t-butyl)], halo($C_{1-4}$ alkyl) (e.g. chloro- or bromo- methyl), hydroxy ($C_{1-4}$ alkyl) (e.g. hydroxymethyl), phenyl, halophenyl (e.g. chlorophenyl), cycloalkyl, nitro, cyano, $C_{1-4}$ alkoxy (e.g. methoxy, ethoxy, propoxy or butoxy), $C_{2-4}$ alkenyloxy (e.g. allyloxy), ($C_{1-4}$ alkylene)dioxy (e.g. methylenedioxy), ($C_{1-4}$ alkoxy) ($C_{1-4}$ alkyl) [e.g. methoxy- or ethoxymethyl or 2-methoxy- or ethoxy-ethyl], mercapto, ($C_{1-4}$ alkyl) thio [e.g. methyl- or ethyl-thio], ($C_{1-4}$ alkyl) sulphonyl [e.g. methyl- or ethyl-sulphonyl], ($C_{1-4}$ haloalkyl)sulphonyl [e.g. trifluoromethylsulphonyl], phenylsulphonyl, unsubstituted or mono- or di-($C_{1-4}$ alkyl) substituted sulphamoyl or carbamoyl, 1-pyrrolidinylsulphonyl, carboxy, ($C_{1-4}$ alkoxy)carbonyl [e.g. methoxy- or ethoxycarbonyl], hydroxy, $C_{1-6}$ alkanoyloxy, benzoyloxy, carboxy ($C_{1-4}$ alkyl)oxy (e.g. carboxymethoxy or 1-carboxyethoxy), unsubstituted or mono- or di-($C_{1-4}$ alkyl) substituted amino, ($C_{1-6}$ alkanoyl)amino, N-($C_{1-4}$ alkyl)-N-($C_{1-6}$ alkanoyl)amino, formylamino, N-($C_{1-4}$ alkyl) formylamino, phenylethyl, methylenedioxyphenyl, phenoxy or benzyloxy. A suitable alkanoyl is acetyl or propionyl. The phenyl group can have more than one substituent; examples of polysubstituted groups are those substituted with up to the maximum possible number (especially 1, 2 or 3) of for example halogen (particularly chlorine) atoms and/or nitro, methyl or methoxy groups.

Examples of suitable phenyl groups are phenyl itself, chlorophenyl (for example o-, m- or p-chlorophenyl), dichlorophenyl (e.g. 3,4-, 2,4-, 3,5- or 2,6-dichlorophenyl), trichlorophenyl (e.g. 2,3,6- or 2,4,5-trichlorophenyl), tetrachlorophenyl, pentachlorophenyl, bromophenyl (e.g. o-, m- or p-bromophenyl), dibromophenyl (e.g. 2,4-dibromophenyl), fluorophenyl (e.g. o-, m- or p-fluorophenyl), difluorophenyl (e.g. 2,4- or 3,4-difluorophenyl), pentafluorophenyl, iodophenyl (e.g. o-iodophenyl), aminophenyl (e.g. p-aminophenyl), methylphenyl (e.g. o-, m- or p-methylphenyl), dimethylphenyl (e.g. 2,6-, 2,5- or 3,4-dimethylphenyl), ethylphenyl (e.g. p-ethylphenyl), propylphenyl (e.g. p-i-propylphenyl), butylphenyl (e.g. p-t-butylphenyl), cyanophenyl (e.g. o-, m- or p-cyanophenyl), nitrophenyl (e.g. o-, m- or p-nitrophenyl), dinitrophenyl (e.g. 2,4-dinitrophenyl), cyanochlorophenyl (e.g. 3-cyano-4-chlorophenyl or 4-cyano-3-chlorophenyl), methylsulphonylphenyl (e.g. p-methylsulphonylphenyl), sulphamoylphenyl (e.g. p-sulphamoylphenyl), N,N-dimethylsulphamoylphenyl [e.g. p-(N,N-dimethylsulphamoyl)phenyl], pyrrolidin-1-ylsulphonylphenyl (e.g. p-pyrrolidin-1-yl-sulphonylphenyl), trifluoromethylsulphonylphenyl (e.g. p-trifluoromethylsulphonylphenyl), methylthiophenyl (e.g. p-methylthiophenyl), (chloromethyl)phenyl [e.g. o-, m- or p-(chloromethyl)phenyl], (bromomethyl)phenyl [e.g. o-, m- or p-(bromomethyl)phenyl], (hydroxymethyl)phenyl [e.g. o-, m- or p-(hydroxymethyl)phenyl], (methoxymethyl)phenyl [e.g. o-, m- or p-(methoxymethyl)phenyl], carboxyphenyl (e.g. o-, m- or p-carboxyphenyl), methoxycarbonylphenyl (e.g. o-, m- or p-methoxycarbonylphenyl), N,N-dimethylcarbamoylphenyl [e.g. o-, m- or p-(N,N-dimethylcarbamoyl)phenyl], N,N-dimethylaminophenyl [e.g. o-, m- or p-(N,N-dimethylamino)phenyl], hydroxyphenyl (e.g. o-, m- or p-hydroxyphenyl), acetoxyphenyl (e.g. o-, m- or p-acetoxyphenyl), benzoyloxyphenyl (e.g. o-, m- or p-benzoyloxyphenyl), (trifluoromethyl)phenyl [e.g. o-, m- or p-(trifluoromethyl)phenyl], methoxyphenyl (e.g. o-, m- or p-methoxyphenyl), dimethoxyphenyl (e.g. 2,4-, 3,4- or 3,5-dimethoxyphenyl), ethoxyphenyl (e.g. o-, m- or p-ethoxyphenyl), propoxyphenyl (e.g. p-i-propoxyphenyl or p-n-propoxyphenyl), butoxyphenyl (e.g. o-, m- or p-i-butoxyphenyl), allyloxyphenyl (e.g. o-, m- or p-allyloxyphenyl), carboxymethoxyphenyl (e.g. o-, m- or p-carboxymethoxyphenyl), 1-carboxyethylphenyl [e.g. o-, m- or p-(1-carboxyethyl)phenyl], chloronitrophenyl (e.g. 3-nitro-4-chlorophenyl), fluoronitrophenyl (e.g. 2-nitro-4-fluorophenyl), chlorofluorophenyl (e.g. 2-fluoro-4-chlorophenyl, 2-chloro-6-fluorophenyl or 2-chloro-4-fluorophenyl), fluorobromophenyl (e.g. 2-fluoro-4-bromophenyl), methylenedioxychlorophenyl (e.g. 2-chloro-4,5-methylenedioxyphenyl), methoxychlorophenyl (e.g. 3-chloro-4-methoxyphenyl), methoxybromophenyl (e.g. 2-methoxy-5-bromophenyl or 3-bromo-4-methoxyphenyl), methoxynitrophenyl (e.g. 2-methoxy-5-nitrophenyl or 4-methoxy-3-nitrophenyl), ethoxynitrophenyl (e.g. 4-ethoxy-3-nitrophenyl), ethoxychlorophenyl (e.g. 4-ethoxy-3-chlorophenyl), ethoxybromophenyl (e.g. 4-ethoxy-3-bromophenyl), benzyloxyphenyl (e.g. p-benzyloxyphenyl), phenylphenyl (e.g. p-phenylphenyl) or methylenedioxyphenylphenyl (e.g. 3,4-methylenedioxyphenylphenyl).

The cycloalkyl group suitably has 3 to 6 carbon atoms; preferably it is cyclopropyl, cyclopentyl, cyclohexyl or methylcyclohexyl.

Preferably the haloalkyl group contains 1 to 3 halogen atoms; examples are 2-chloroethyl, trifluoromethyl or trichloromethyl.

The halogen can be fluorine, chlorine, bromine or iodine.

Suitable salts are salts with inorganic or organic acids, e.g. hydrochloric, nitric, sulphuric, toluenesulphonic, acetic or oxalic acid. The esters are suitably alkanoates (e.g. acetates) and the ethers are suitably alkyl (e.g. methyl or ethyl), aryl (e.g. phenyl) or aralkyl (e.g. benzyl) ethers.

The metal complex is suitably one including copper, zinc, manganese or iron. It preferably has the general formula:

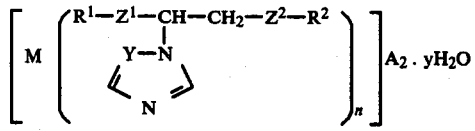

wherein Y, $R^1$, $R^2$, $Z^1$ and $Z^2$ are as defined above, M is a metal, A is an anion (e.g. a chloride, bromide, iodide, nitrate, sulphate or phosphate anion), n is 2 or 4 and y is 0 or an integer of 1 to 12.

Examples of the triazole compounds of general formula (I) are given in Table I.

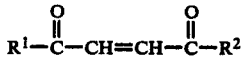

where $R^1$ and $R^2$ are as defined above.

The reduction of the diketone generally involves dissolving the reactants in a solvent such as diethyl ether or tetrahydrofuran (for lithium aluminium hydride reduction) or water (for sodium borohydride reduction). The temperature at which the reaction may be carried out will depend on the reactants and solvents but generally the reaction mixture is heated under reflux. The reaction product is then isolated by for example extraction into a convenient solvent after acidification with a dilute mineral acid. After removal of the solvent in vacuo, the product may be crystallised from a convenient solvent.

The compounds of general formula (III) may be made by any of the methods set out in the literature.

The salts, metal complexes, ethers, esters and silyl ethers of the compounds of general formula (I) can be prepared from the latter in known manner. For example, the complexes can be made by reacting the uncomplexed compound with a metal salt in a suitable solvent. The substituent on the phenyl group in the compound of general formula (I) can often be changed by methods known in the art. For example, a compound wherein for

TABLE I

| COMPOUND NO | $R^1$ | $R^2$ | $Z^1$ | $Z^2$ | MELTING POINT (°C.) |
|---|---|---|---|---|---|
| 1 | t-Bu | t-Bu | CHOH | C=O | 95°–96° |
| 2 | $C_6H_5$ | $C_6H_5$ | CHOH | C=O | 166°–167° |
| 3 | p-Cl—$C_6H_4$ | p-Cl—$C_6H_4$ | CHOH | C=O | 97°–98° |
| 4 | 2,4-diCl—$C_6H_3$ | 2,4-diCl—$C_6H_3$ | CHOH | C=O | |
| 5 | i-Pr | i-Pr | CHOH | C=O | |
| 6 | i-Pr | p-Cl—$C_6H_4$ | CHOH | C=O | 116° |
| 7 | i-Pr | o-Cl—$C_6H_4$ | CHOH | C=O | |
| 8 | i-Pr | p-MeO—$C_6H_4$ | CHOH | C=O | |
| 9 | i-Pr | o-MeO—$C_6H_4$ | CHOH | C=O | |
| 10 | t-Bu | p-Cl—$C_6H_4$ | CHOH | C=O | |
| 11 | t-Bu | o-Cl—$C_6H_4$ | CHOH | C=O | |
| 12 | t-Bu | p-MeO—$C_6H_4$ | CHOH | C=O | |
| 13 | t-Bu | o-MeO—$C_6H_4$ | CHOH | C=O | |

The compounds, salts and complexes of the invention may be made by selectively reducing a diketone of general formula (II):

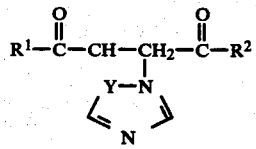

wherein Y, $R^1$ and $R^2$ are as defined above, or a salt or metal complex thereof, with for example a metal hydride reducing agent (e.g. lithium aluminium hydride or sodium borohydride) in an inert polar solvent (e.g. diethyl ether, water or ethanol).

The diketone starting materials may be made by reacting imidazole or 1,2,4-triazole or a salt thereof with the appropriate unsaturated γ-diketone in a high boiling hydrocarbon solvent (e.g. toluene or xylene) at refluxing temperatures. Thus for example 1,2,4-triazole may be reacted with a compound of general formula (III):

example $R_1$ is phenyl substituted with carboxy can be prepared from the corresponding compound wherein $R_1$ is phenyl substituted with alkoxycarbonyl, and vice-versa.

The compounds are active fungicides, particularly against the diseases:

*Pyricularia oryzae* on rice

*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants

*Plasmopara viticola* on vines

*Erysiphe graminis* (powdery mildew) on barley and wheat and other powdery mildews on various hosts such as Helminthosporium spp. on cereals, *Sphaerotheca fuliginea* on cucurbits (e.g. cucumber), *Podosphaera leucotricha* on apples and *Uncinula necator* on vines

*Cercospora arachidicola* on peanuts and other Cercospora species on for example sugar beet, bananas and soya beans

*Botrytis cinerea* (grey mould) on tomatoes, strawberries, vines and other hosts

*Phytophthora infestans* (blight) on tomatoes

*Venturia inaequalis* (scab) on apples

Some of the compounds have also shown a broad range of activities against fungi in vitro. They have activity against various post-harvest diseases on fruit (e.g. *Penicillium digatatum* and *italicum* on oranges and *Gloeosporium musarum* on bananas). Further some of the compounds are active as seed dressings against: Fusarium spp., Septoria spp., Tilletia spp. (i.e. bunt, a seed borne disease of wheat), Ustilago spp., Helminthosporium spp. on cereals, *Rhizoctonia solani* on cotton and *Corticium sasakii* on rice.

The compounds also have plant growth regulating activities.

The plant growth regulating effects of the compounds are manifested as for example a stunting or dwarfing effect on the vegetative growth of woody and herbaceous mono- and di-cotyledonous plants. Such stunting or dwarfing may be useful, for example, in peanuts, cereals and soya bean where reduction in stem growth may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus*, *Lolium multiflorum* and *perenne*, *Agrostis tenuis*, *Cynodon dactylon* (Bermuda grass), *Dactylis glomerata*, Festuca spp. (e.g. *Festuca rubra*) and Poa spp. (e.g. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in for example grasses. The compounds can also stunt weed species present in the grasses; examples of such weed species are sedges (e.g. Cyperus spp.) and dicotyledonous weeds (e.g. daisy, plantain, knotweed, speedwell, thistle, docks and ragwort). The growth of non-crop vegetation (e.g. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful for example for improving the quality of a sward by preferential suppression of the growth of undesirable species.

The dwarfing may also be useful in miniaturising ornamental, household, garden and nursery plants (e.g. poinsettias, chrysanthemums, carnations, tulips and daffodils).

As indicated above, the compounds can also be used to stunt woody species. This property can be used to control hedgerows or to shape fruit trees (e.g. apples). Some coniferous trees are not significantly stunted by the compounds so the compounds could be useful in controlling undesirable vegetation in conifer nurseries.

The plant growth regulating effect may (as implied above) manifest itself in an increase in crop yield.

In the potato, vine control in the field and inhibition of sprouting in the store may be possible.

Other plant growth regulating effects caused by the compounds include alteration of leaf angle and promotion of tillering in monocotyledonous plants. The former effect may be useful for example in altering the leaf orientation of, for example, potato crops thereby letting more light into the crops and inducing an increase in phytosynthesis and tuber weight. By increasing tillering in monocotyledonous crops (e.g. rice), the number of flowering shoots per unit area may be increased thereby increasing the overall grain yield of such crops. In grass swards an increase in tillering could lead to a denser sward which may result in increased resilience in wear.

The treatment of plants with the compounds can lead to the leaves developing a darker green colour.

The compounds may inhibit, or at least delay, the flowering of sugar beet and thereby may increase sugar yield. They may also reduce the size of sugar beet without reducing significantly the sugar yield thereby enabling an increase in planting density to be made. Similarly in other root crops (e.g. turnip, swede, mangold, parsnip, beetroot, yam and cassava) it may be possible to increase the planting density.

The compounds could be useful in restricting the vegetative growth of cotton thereby leading to an increase in cotton yield.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below the snow cover during the cold weather. Further the compounds may cause drought or cold resistance in certain plants.

When applied as seed treatments at low rates the compounds can have a growth stimulating effect on plants.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. However, on certain plants even application rates within these ranges may give undesired phytotoxic effects. Routine tests may be necessary to determine the best rate of application of a specific compound for any specific purpose for which it is suitable.

The compounds may be used as such for fungicidal or plant growth regulating purposes but are more conveniently formulated into compositions for such usage. The invention thus provides also a fungicidal or plant growth regulating composition comprising a compound of general formula (I) or a salt, complex, ether or ester thereof as hereinbefore defined, and a carrier or diluent.

The invention also provides a method of combating fungal diseases in a plant, which method comprises applying to the plant, to seed of the plant or to the locus of the plant or seed a compound or salt, complex, ether or ester thereof as hereinbefore defined.

It also provides a method of regulating the growth of a plant, which method comprises applying to the plant, to seed of the plant or to the locus of the plant or seed a compound or salt, complex, ether or ester thereof as hereinbefore defined.

The compounds, salts, complexes, ethers and esters can be applied in a number of ways, for example they can be formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound, are preferred. Such granules suitably contain up to 25% by weight of the compound. The invention therefore also provides a fertiliser composition comprising the compound of general formula (I) or a salt, metal complex, ether or ester complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). These concentrates suitably contain organic acids (e.g. alkaryl or aryl sulphonic acids such as xylenesulphonic acid or dodecylbenzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal or plant growth regulating activity or compounds having herbicidal or insecticidal activity.

The other fungicidal compound can be for example one which is capable of combating ear diseases or cereals (e.g. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim (BCM), thiophanate-methyl, captafol, captan, sulphur, dithiocarbamates, carbathiins, copper oxychloride, triforine, dodemorph, tridemorph, dithianon, pyrazophos, binapacryl, quinomethionate, panoctine, furalaxyl, aluminium tris(ethylphosphonate), DPX3217, ethirimol, dimethirimol, bupirimate, chlorothalonil and metaxanine.

Suitable insecticides are pirimor, croneton, dimethoate, metasystox and formothion.

The other plant growth regulating compound can be one which controls weeds or seedhead formation, improves the level or longevity of the plant growth regulating activity of the compounds of general formula (I), selectively controls the growth of the less desirable plants (e.g. grasses) or causes the compound of general formula (I) to act faster or slower as a plant growth regulating agent. Some of these other agents will be herbicides. Examples of suitable agents are the gibberellins (e.g. GA$_3$, GA$_4$ or GA$_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or BAP), phenoxyacetic acids (e.g. 2,4-D or MCPA), substituted benzoic acids (e.g. TIBA), morphactins (e.g. chlorfluorecol), maleic hydrazide, glyphosate, glyphosine, long chain fatty alcohols and acids (e.g. Off Shoot O or Off Shoot T), dikegulac, Sustar, Embark, substituted quaternary ammonium and phosphonium compounds (e.g. CCC or Phosfon-D), Ethrel, carbetamide, Racuza, Alar, asulam, abscissic acid, isopyrimol, RH531, hydroxybenzonitriles (e.g. bromoxynil), Avenge, Suffix or Lontrel.

The following Examples illustrate the invention; the temperatures are given in degrees Centigrade (°C.).

EXAMPLE 1

4-(1,2,4-Triazol-1-yl)-2,2,7,7-tetramethyl-octan-3-ol-6-one (Compound 1)

Stage 1: 2,2,7,7-tetramethyl-oct-4-en-3,6-dione, m.p. 107-109°, was prepared according to the method of Ramasseul and Rassat, Bull. Soc. Chim. Fr., 1963, p. 2214-2217.

Stage 2: 2,2,7,7-tetramethyl-oct-4-en-3,6-dione (0.01 mol) and 1,2,4-triazole (0.01 mol), suspended in toluene (100 ml), were refluxed for 24 hours. On cooling to room temperature, the organic layer was washed with water (4×100 ml) and dried over sodium sulphate. Removal of the solvent gave 4-(1,2,4-triazol-1-yl)-2,2,7,7-tetramethyl-octan-3,6-dione, m.p. 66°-69°.

Stage 3: 4-(1,2,4-triazol-1-yl)-2,2,7,7-tetramethyl-octan-3,6-dione (0.005 mol) was dissolved in methanol (50 ml). Sodium borohydride (0.005 mol) was added portionwise at room temperature for 2 hours, the solution was refluxed for 1½ hours. Removal of the methanol gave a white solid which was dissolved in dilute hydrochloric acid (50 ml) and the solution extracted into chloroform (50 ml), washed with saturated sodium bicarbonate (50 ml) and with water (2×100 ml) and dried over anhydrous sodium sulphate. Removal of the chloroform gave a colourless oil which was crystallised from petroleum ether/chloroform to give the title compound as a white crystalline solid, m.p. 95°-96°.

EXAMPLE 2

The compounds were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots.

The test compounds were formulated either by bead-milling with aqueous Dispersol T or as a solution in acetone/ethanol which was diluted to the required concentration immediately before use. For the foliage diseases, 100 p.p.m. a.i. suspensions were sprayed on to the foliage and applied to the roots of the same plant via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil (roots) and to the foliage (by spraying) one or two days before the plant was inoculated with the diseases. An exception was the test on *Erysiphe graminis*, in which the plants were inoculated 24 hours before treatment. After inoculation, the plants were put into an appropriate environment to allow infection to take place and then incubated until the disease was ready for assessment. The period between inoculation and assessment varied from 4 to 14 days according to the disease and environment.

the disease control was recorded by the following grading:
 4=No disease
 3=0-5%
 2=6-25%
 1=26-60%
 0=>60%

The results are shown in Table II.

TABLE II

| COMPOUND NUMBER | PUCCINIA RECONDITA (WHEAT) | PHYTOPHTHORA INFESTANS (TOMATO) | PLASMOPARA VITICOLA (VINE) | PIRICULARIA ORYZE (RICE) | BOTRYTIS CINEREA (TOMATO) | ERYSIPHE GRAMINIS (BARLEY) | CERCOSPORA ARACHIDICOLA (PEANUT) |
|---|---|---|---|---|---|---|---|
| 1 | 3 | 2 | 0 | 3 | 1-2 | | 3 |
| 2 | | | | | | | |
| 3 | | | | | | | |

TABLE II-continued

| COMPOUND NUMBER | PUCCINIA RECONDITA (WHEAT) | PHYTOPHTHORA INFESTANS (TOMATO) | PLASMOPARA VITICOLA (VINE) | PIRICULARIA ORYZE (RICE) | BOTRYTIS CINEREA (TOMATO) | ERYSIPHE GRAMINIS (BARLEY) | CERCOSPORA ARACHIDICOLA (PEANUT) |
| --- | --- | --- | --- | --- | --- | --- | --- |
| 4 | | | | | | | |
| 5 | | | | | | | |
| 6 | | | | | | | |
| 7 | | | | | | | |
| 8 | | | | | | | |
| 9 | | | | | | | |
| 10 | | | | | | | |
| 11 | | | | | | | |
| 12 | | | | | | | |

We claim:
1. A compound of formula:

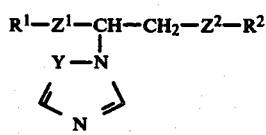

wherein each of $R^1$ and $R^2$, which may be the same or different, is $C_{3-6}$ cycloalkyl optionally substituted with one methyl, $C_{1-5}$ alkyl optionally substituted with up to three halogeno or phenyl optionally substituted with up to three substituents selected from the class consisting of halogen, $C_{1-5}$ alkyl, $C_{1-5}$ alkoxy or nitro, Y is =N— and one of $Z^1$ and $Z^2$ is C=O and the other is —CH(OH)—.

2. A compound as claimed in claim 1 wherein $R^1$ is propyl, butyl, phenyl or mono- or di-chlorophenyl.

3. A compound as claimed in claim 2 wherein $R^1$ is i-propyl, t-butyl, phenyl, p-chlorophenyl or 2,4-dichlorophenyl.

4. A compound as claimed in claim 1 wherein $R^2$ is propyl, butyl, phenyl, mono- or di-chlorophenyl or monomethoxyphenyl.

5. A compound as claimed in claim 4 wherein $R^2$ is i-propyl, t-butyl, phenyl, o- or p-chlorophenyl, 2,4-dichlorophenyl or o- or p-methoxyphenyl.

6. A compound as claimed in claim 1 wherein $Z^1$ is CH(OH) and $Z^2$ is C=O.

7. A compound as claimed in claim 1 which is 4-(1,2,4-triazol-1-yl)-2,2,7,7-tetramethyloctan-3-ol-6-one.

8. A fungicidal or plant growth stunting composition consisting essentially of, as active ingredient, a fungicidally effective amount or a plant growth regulating amount of a compound as claimed in claim 1, and a carrier for the active ingredient.

9. A method of combating fungal diseases in, or for stunting the growth of, a plant, the method comprising applying to the plant, to seed of the plant or to the locus of the plant or seed, a fungicidally effective amount of a plant growth stunting amount of a compound according to claim 1.

* * * * *